United States Patent [19]

Yuhas, deceased et al.

[11] Patent Number: 4,742,050

[45] Date of Patent: May 3, 1988

[54] SENSITIZATION OF HYPOXIC TUMOR CELLS AND CONTROL OF GROWTH THEREOF

[75] Inventors: John M. Yuhas, deceased, late of Bala Cynwyd, by Mary Ellen Yuhas, administrator; Robert L. Goodman, Gladwyne, all of Pa.; Robert E. Moore, Wilmington, Del.

[73] Assignee: Adamantech, Inc., Linwood, Pa.

[21] Appl. No.: 96,298

[22] Filed: Sep. 9, 1987

Related U.S. Application Data

[60] Continuation of Ser. No. 724,445, Apr. 17, 1985, abandoned, Division of Ser. No. 580,760, Feb. 17, 1984, abandoned, which is a continuation-in-part of Ser. No. 517,150, Jul. 25, 1983, abandoned, which is a continuation-in-part of Ser. No. 408,589, Aug. 17, 1982, abandoned.

[51] Int. Cl.$^4$ .............................................. A61K 31/70
[52] U.S. Cl. ........................................................... 514/34
[58] Field of Search ........................................... 514/34

[56] References Cited

U.S. PATENT DOCUMENTS

| | | | |
|---|---|---|---|
| 3,453,333 | 7/1969 | Litt et al. | 260/614 |
| 3,778,381 | 12/1973 | Rosano et al. | 424/342 |
| 3,828,085 | 8/1974 | Price et al. | 424/320 |
| 4,241,060 | 12/1980 | Smithen | 424/248.57 |
| 4,282,232 | 8/1981 | Agrawal | 424/267 |
| 4,325,972 | 4/1982 | Geyer et al. | 424/325 |
| 4,366,169 | 12/1982 | White | 424/285 |

FOREIGN PATENT DOCUMENTS 89815  9/1983  European Pat. Off. .

OTHER PUBLICATIONS

"Radiopaque Applications of Brominated Fluorocarbon Compounds in Expermimental Animals and Human Subjects," D. M. Long et al., appearing in Biochemistry Involving Carbon-Fluorine Bonds, edited by R. Filler, ACS Symposium Series No. 28, 171-189, (1976).

Chemical Abstracts, vol. 87, No. 23, Dec. 5, 1977, p. 278, No. 181618x, Columbus, Ohio, U.S.A., T. Matsumoto et al.: "Role on Oncotic Agents in Saving Effect of Perfluorochemical Emulsions in Hemodilution" Chem. Pharm. Bull., 1977, 25 (9), 2163-2171.

Chemical Abstract, vol. 79, No. 13, Oct. 1, 1973, p. 45, No. 73792a, Columbus, Ohio, U.S.A., R. Esaki et al.: "Sensitivity of Anticancer Drugs and Their Concentration in Tissues" Advan. Antimicrob. Antineoplastic Chemother. Proc. Int. Congr. Chemother., 7th 1971, (Pub. 1972), 2, 383-386.

Chemical Abstracts, vol. 97, No. 11, Sep. 13, 1982, p. 55, No. 84920p, Columbus, Ohio, U.S.A., T. Kokunai et al.: "Effect of Perfluorochemicals on BCNU Chemotherapy in a Rat Brain-Tumor Model" Brain Nerve, 1982, 34(6), 609-615.

Chemical Abstracts, vol. 97, No. 23, 6th Dec. 1982, pp. 26, 27, No. 192822a, Columbus, Ohio, U.S.A., J. Neurosurg., 1982, 57(4), 467-471.

Chemical Abstracts, vol. 96, No. 12, Mar. 1982, pp. 400, 401, No. 91568n, Columbus, Ohio, U.S.A., A. N. Markina et al.: "Emulsifying Capacity of Sodium Deoxycholate in Regards to Perfluorocarbons in the Aqueous Phase" Perftorirovannye Uglerody Biol. Med. 1980, 67-75.

The Merck Index, 1976, pp. 359, 371, 782, 1282.

*Primary Examiner*—Stanley J. Friedman
*Attorney, Agent, or Firm*—J. Edward Hess; Donald R. Johnson

[57] ABSTRACT

Method of sensitizing hypoxic tumor cells to radiotherapy and chemotherapy by contacting the cells or the vasculature thereof with an aqueous dispersion of an oxygen carrying perfluoro compound and a dispersant for the compound, and sensitizing chemotherapeutic and protective compositions therefor.

30 Claims, No Drawings

SENSITIZATION OF HYPOXIC TUMOR CELLS AND CONTROL OF GROWTH THEREOF

RELATED APPLICATIONS

This application is a continuation of application Ser. No. 724,445, filed Apr. 17, 1985, now abandoned. This application is a division of U.S. application Ser. No. 580,760, filed Feb. 17, 1984; the latter being a continuation-in-part of U.S. application Ser. No. 517,150, filed July 25, 1983, and now abandoned; which in turn was a continuation-in-part of U.S. application Ser. No. 408,589, filed Aug. 17, 1982, and all are now abandoned.

BACKGROUND OF THE INVENTION

This invention relates to the sensitization of hypoxic tumor cells to therapy, and in particular to methods, compositions and systems for sensitizing hypoxic tumor cells to radiation and/or to certain chemotherapeutic agents, whether the therapy is employed alone or in combination with agents which protect normal tissues from injury. The invention further relates to diagnostic methods in support of the sensitization and therapy.

For convenience of expression in this specification the following or similar terms are sometimes abbreviated as indicated:
"PFC"-perfluoro compound
"RS"-radiosensitization or radiosensitizing
"RT"-radiotherapy or radiotherapeutic
"CT"-chemotherapy or chemotherapeutic
"RP"-radioprotection or radioprotective
"CTP"-chemotherapeutic protective
"RI"-radioimaging Oxygen deficient (hypoxic) cells can be up to about three times more resistant to radiation than are well-oxygenated cells. These cells are relatively common in tumors but are rare in normal tissues, thereby giving the tumor cells a greater resistance to radiation than one observes in normal tissues. As a consequence, one often cannot deliver enough radiation to eradicate the tumor cells without incurring an unacceptably high risk of severe injury to normal tissue. These same hypoxic cells are often resistant to those forms of chemotherapy which are oxygen dependent. In such chemotherapy, however, oxygen must often be supplied to the hypoxic cells for another reason in addition to maximal cell destruction: hypoxic cells are not actively growing (multiplying) and many of the more effective chemotherapeutic drugs cannot kill the cells unless they are growing. Further, hypoxic cells have low energy reserves and are thus believed less able to actively transport certain chemotherapeutic drugs across their membranes.

The following contribute to the relatively common occurrence of hypoxic cells in tumors: the tumors outgrow their blood supply; blood flow through the vessels in the tumor is sluggish; and the tumor cells near the blood vessels consume large amounts of oxygen, thereby even further reducing the amount available to more distant cells. If means could be developed to re-oxygenate these hypoxic areas one would expect large increases in radiosensitivity because the hypoxic tumor regions are near the minimum of oxygen dependent radiosensitivity. The same does not hold true for normal tissues, since, under natural conditions, they are already near the maximum for oxygen dependent radiosensitivity. The same or similar considerations also apply in sensitizing cells to chemotherapy.

An obvious approach to reversing the resistance of hypoxic cells to treatment is to directly supply the cells with more oxygen. This was initially attempted by injecting hydrogen peroxide which would hopefully release oxygen at the tumor site. The technique has never achieved practicality, however, due to the toxicity of injected hydrogen peroxide.

A potentially less toxic, but similarly direct approach, involved having the patient breathe 100% oxygen at 3 atmospheres pressure both before and during radiotherapy. While at least some results were encouraging, the toxicity of hyperbaric oxygen treatments has limited the use of this technique to sub-optimal treatments, i.e., fewer but larger radiation doses.

A third direct approach was initially tested by Belgrad et al (*Radiology* 133: 235–237, 1979). These investigators oxygen-saturated a pure sample of perfluorooctyl bromide, known as a highly efficient oxygen carrier, and injected the oxygenated, neat compound into mice bearing the P388 leukemia. Twenty-four hours later they exposed the mice to graded doses of whole body X-rays, and compared the survival time of these mice to similarly treated mice which had received an injection of a salt solution. The results of these studies failed to show a significant improvement in therapy, and local toxic reactions in the peritoneal cavity were observed.

The Belgrad et al study is not useful as a guide or suggestion of the use of perfluorooctyl bromide or other PFC in hypoxic tumor cell therapy. The study has little clinical relevance, and discourages further studies leading to clinical investigations. One would never consider flooding (as opposed to local administration) the peritoneal cavity with a pure PFC or even a PFC in emulsified form. Further, oxygenation of a PFC prior to administration coupled with radiation treatment 24 hours after administration offers almost no opportunity for the leukemic cells to be sensitized to radiation. Lastly, the highest irradiation doses reported by Belgrad et al are known to be lethal to mice, and thus leave open to conjecture whether the perfluorooctyl bromide had any sensitizing effect at all under such conditions.

In attempts to sidestep oxygen delivery as the primary mode of radiosensitization, radiations have been used which are less dependent on the oxygenation status of the cell for their cell killing efficiency. Such radiations are densely ionizing or high LET radiations and have been limited, however, by their unfavorable focusing characteristics. Normal tissues receive more of these radiations per unit dose delivered to the tumor than is the case with conventional radiations, and this factor has counterbalanced the expected advantage due to independence of oxygenation state. Another radiosensitization technique for avoiding gross oxygenation is the use of drugs which mimic the presence of oxygen but which can diffuse further into the tumor because they are less readily consumed by the cells traversed. Typical of such drugs are metronidazole, misonidazole and the nitroimidazole compounds disclosed in U.S. Pat. Nos. 4,241,060 and 4,282,232. Such drugs, while initially promising, have not produced large therapeutic gains clinically because the drug doses required to produce significant radiosensitization also produce unacceptable neurotoxicity in patients.

Hypoxia is invariably found in carcinoma and sarcoma but even in benign conditions (where the hypoxic cell tumors are not continually increasing in mass), radiotherapy and/or chemotherapy are sometimes prescribed in order to forestall cancerous conditions. The present invention is therefore applicable both to malignant and benign hypoxic tumor cells.

As indicated in Belgrad et al, perfluorinated hydrocarbons are known which are good oxygen carriers and some have been used as blood substitutes. Nevertheless, this property alone cannot make these useful as sensitizing agents in radiotherapy and/or oxygen-dependent chemotherapy. In addition to good oxygen transfer capability such compounds, for effective RS and/or CTS effect, must:

1. Be capable of rapid transfer to the dense cell populations characterizing hypoxic tumor cells or to the vasculature thereof, and of releasing oxygen to these cells;

2. Exhibit favorable residence time in a mammalian system, as opposed to too rapid elimination by excretion, transpiration or metabolism, and as opposed to undue accumulation in the system (as in the liver and spleen); and 3. Exhibit no toxicity or tolerable toxicity to normal (euoxic) cells.

Ideally, the oxygen transfer compound, if used systemically, will diffuse quickly through the vasculature, pick up oxygen in the lungs, remain in the cardiovascular system for about 10 to 12 days, (to permit periodic irradiation at controlled dosages) and then be rapidly eliminated, while producing no intolerable toxicity. Under such conditions sensitization to radiotherapy and/or chemotherapy can be maximized. However, residence times as short as 2 to 8 hours may be sufficient if only short term therapy is necessary. Hence, considerable leeway should be possible in treatment protocols, depending on the types, state of division and site of the tumor cells, and other considerations known to therapists, such as type of irradiation or chemotherapeutic agent, side effects, and mode of administration.

SUMMARY OF THE INVENTION

In accordance with the present invention effective sensitization of hypoxic tumor cells, as a prelude to highly beneficial radiotherapy and/or oxygen-dependent chemotherapy, is achieved by contacting the cells or vasculature thereof with an oxygen carrying perfluoro compound, wherein the perfluoro compound is uniformly dispersed in small particle size in an aqueous medium. The resulting aqueous dispersion is rendered isotonic (or otherwise physiologically acceptable) to mammalian cells prior to use as a sensitizing agent by the addition of salts, buffering agents or other reagents known to be effective for this purpose.

In one aspect of the invention the dispersion is injected intravenously, is carried through the lungs where it picks up oxygen, and then penetrates the region of the hypoxic tumor cells. The oxygen transferred from the perfluoro compound to the hypoxic cells sensitizes the cells. Simultaneously with the sensitization or thereafter, the cells are irradiated and/or a CT agent is administered. Cell destruction or reduced rate of growth can be monitored by biopsy, radioimaging or other technique. ("Growth" as used herein means cell multiplication; "control of growth" or similar term means cell destruction or decreased growth rate.)

In another aspect of the invention, the hypoxic tumor cells are oxygenated hyperbarically but at oxygen pressures and/or for periods substantially less severe than conventionally employed for treatment of hypoxia, and contact of the cells or vasculature thereof with the perfluoro compound thus supplements oxygen transfer to the cells. This enhanced sensitization is then followed or accompanied by irradiation or chemotherapy in the conventional manner.

In still another (diagnostic) aspect of the invention, penetration of the perfluoro compound into the regions of the hypoxic tumor cells is monitored by systemic administration of a perfluoro compound which also has radiopaque properties, thereby permitting radioimaging. A variation of this approach is to incorporate into a dispersion containing an oxygen carrying perfluoro compound which does not have radioimaging properties, another compound which is an RI agent, thereby rendering the hypoxic cells susceptible to radioimaging.

In other aspects of the invention, RP and/or CTP agents are combined with the oxygen carrying PFC in the dispersion, or are separately delivered to the site of the hypoxia, in order to afford additional therapeutic response. This effect is achieved through the ability of the perfluoro compound to sensitize the tumor cells, while the RP and CTP agents, since they are not absorbed by the tumor cells, shield the normal tissues from attack by radiation and the CT agents, respectively. In some cases the same agent can be both radioprotective and chemotherapeutic protective.

The term "mammal" or similar term as used throughout this specification is intended in its broad and equivalent sense to mean and include all animals.

DETAILED DESCRIPTION

The Sensitizer Dispersions

The sensitizing agent of the invention is an aqueous dispersion of an oxygen carrying perfluoro compound and a dispersant (surfactant or emulsifier) which is effective for uniformly dispersing the perfluoro compound in the aqueous medium. The dispersant is required because the perfluoro compounds are relatively hydrophobic and would otherwise tend to agglomerate in the mammalian body fluids through which the compound must pass and which serve to carry the compond to the hypoxic tumor cells or vasculature thereof. Thus, although the perfluoro compound in the neat state might initially be injectable into the body, in a short time its tendency to agglomerate would impede its use as a sensitizer. The aqueous dispersion medium also permits addition of reagents for rendering the dispersion isotonic or otherwise physiologically acceptable to the cells.

Generally, the perfluoro compounds and dispersions thereof useful in this invention are those materials identified in the patent and other technical literature as synthetic blood substitutes. Representative of the patent literature disclosing such blood substitutes are U.S. Pat. Nos. 3,641,167, 3,823,091, 3,911,138, 3,962,439 3,993,581, 4,041,086, 4,105,798, and 4,325,972, the disclosures of which are incorporated herein by reference.

It will be apparent from a review of the foregoing patents and other literature that a wide variety of perfluorinated compounds when suitably dispersed in an aqueous medium can be used for the purposes of the present invention. The perfluoro compounds thus include aliphatic (acyclic or cyclic) and aromatic compounds, whether perfluorinated hydrocarbons only or also containing heteroatoms such as oxygen, sulfur and/or nitrogen, and may be used singly or as mixtures of two or more. The selection of perfluoro compound for use in specific cases in accordance with the invention will depend on a variety of factors, including whether the treatment is in conjunction with radiotherapy, chemotherapy, or both; the character and locus of the hypoxia; the potency of the perfluoro compound as a sensitizer; toxicity of the perfluoro compound to normal cells and to the host mammal; capability of forming sufficiently small particle size dispersions and sufficiently stable dispersions to diffuse rapidly to the region of the hypoxic cells; residence time in the mammal, including accumulation tendencies; and similar considerations familiar to those knowledgeable in the sensitization art. Guidance for such selection can be obtained from the blood substitute art, particularly as to oxygen transport capability, dispersion particle size and stability, mammalian residence time, and cytotoxicity. Additionally, on the basis of the in vitro and in vivo studies reported and discussed hereinafter, guidance is provided for selection of perfluoro compound and treatment parameters in specific cases of sensitization.

"Perfluoro compound" or "perfluorocarbon" as used herein refers to a substantially fluorinated or completely fluorinated material which is generally but not necessarily a liquid at ambient temperature and pressure. "Substantially fluorinated" as used herein means that most of the hydrogen atoms of a compound have been replaced by fluorine atoms, such that further replacement does not substantially increase the oxygen transport capability of the material. It is believed that this level is reached when at least 80-90% of the hydrogen atoms have been replaced by fluorine atoms. However, it is preferred that at least 95% of the hydrogen atoms have been replaced, more preferably at least 98% and most preferably, 100%. In the aforementioned U.S. Pat. Nos. 3,911,138 and 4,105,798, the ability to transport oxygen is related to the solubility in the materials of a gas such as oxygen. These patents suggest that the perfluorinated materials will absorb 10–100 cc of oxygen per 100 cc of material at 25° C. and 760 milliliters of mercury.

Representative of the perfluoro compounds preferred for use in this invention are the perfluorinated derivatives of chemically inert $C_9$–$C_{18}$ polycyclic compounds such as bicyclononanes (e.g., bicyclo[3.3.1]nonane, 2,6-dimethylbicyclo[3.3.1]nonane, 3-methylbicyclo[3.3.1]nonane and trimethylbicyclo[3.3.1]nonane); adamantane and alkyl ($C_1$–$C_6$) adamantanes such as methyl and dimethyladamantane, ethyl and diethyladamantane, trimethyladamantane, ethylmethyladamantane, ethyldimethyladamantane and triethyladamantane; methyldiadamantane and trimethyldiadamantane; methyl and dimethylbicyclooctanes; tetrahydrobinor-S, pinane, camphane, decalin and alkyl decalins such as 1-methyldecalin; and 1,4,6,9-dimethanodecalin; bicyclo[4.3.2]undecane, bicyclo[5.3.0]decane, bicyclo[2.2.1]octane, tricyclo[5.2.1.0$^{2,6}$]decane, methyltricyclo[5.2.1.0$^{2,6}$]decane, and the like; or any mixtures thereof. Hetero atom perfluoro compounds include F-tributyl amine, F-tripropyl amine and F-N,N-dimethylcyclohexylmethylamine; perfluoro ethers such as F-2-butyltetrahydrofuran, F-2-butylfuran, F-hydrofuran, the 1,2,2,2-tetrafluoromethyl ether of F-(2,5,8-trimethyl-3,6,9-trioxa-1-dodecanol), F-N-methyldecahydroquinoline, F-1-methyloctahydroquinolizine, F-octahydroquinolidine and F-N-cyclohexylpyrrolidine. Aromatic and aliphatic compounds include F-naphthalene, F-1-methyl-napthalene, F-n-methyl-morpholine, F-n-heptane and 1,2-bis-nonylfluorobutylethylene.

Certain of the fluorine atoms of the foregoing materials may be substituted by other halogen atoms such as bromine. Included among these compounds, are, for example, monobrominated compounds such as 1-bromopentadecafluoro-4-isopropylcyclohexane, 1-bromotridecafluoro-hexane, 1-bromo-pentadecafluorooctane and 1-bromo-pentadecafluoro-3-isopropylcyclopentane and perfluoro-1-bromobutylisopropyl ether, or polybrominated derivatives thereof.

When bromo or iodo atoms appear in the perfluoro compounds, the compounds tend to be radiopaque while also retaining a large measure of their oxygen transporting capabilities. The radiopacity renders these compounds useful as radioimaging (RI) agents, and therefore these compounds in some cases can be used not only as sensitizing agents but also as RI agents, alone or in combination with other sensitizers and/or RI agents.

It is known that the rate of transpiration of perfluorinated hydrocarbons from lower mammals is in the order: tricyclics > bicyclics > alkyl monocyclics > paraffinics. Accordingly, where high rate of transpiration is preferred, for example when only a brief interval of irradiation is prescribed, a tricyclic perfluoro compound will be preferred over other perfluoro compounds. Conversely, if extended radiotherapy or chemotherapy is desired, therefore requiring longer sensitizer residence time, a bicyclic or monocyclic perfluoro compound might be chosen.

The more preferred perfluoro compounds for use in the invention on the basis of relative inertness (chemical and biological), good dispersability and residence time are the perfluoro $C_9$–$C_{18}$ polycyclic hydrocarbons of U.S. Pat. NO. 4,105,798, and particularly F-dimethyladamantane, F-trimethylbicyclononane, F-tricyclo[5.2.1.0$^{2,6}$]decane, F-methyltricyclo[5.2.1.0$^{2,6}$]decane, F-bicyclo[5.2.0]decane and F-methylbicyclo[5.2.0]decane, including any isomers thereof, and mixtures of such compounds, for example mixtures of F-dimethyladamantane and F-trimethylbicyclononane, ranging from about 90/10 to 10/90 by weight.

The preferred dispersants for uniformly dispersing the perfluoro compounds in an aqueous medium are the nonionic surfactants. In some compositions and systems of the invention, particularly those cases where the dispersions are used non-systemically, such as in topical or local treatments, ionic or amphoteric surfactants may be used to disperse the perfluoro compounds. Because systemic treatments require careful attention to physiological acceptability of the compounds, such as isotonic character, ionic surfactants are less desirable, although it is possible to offset or moderate their ionic character by formulating the dispersions with electrolytes or other additives.

Suitable nonionic surfactants include aliphatic materials such as block copolymers of ethylene oxide and propylene oxide comprising a hydrophobic propylene oxide section combined with one or more hydrophilic ethylene oxide sections, for example the "Pluronic" (trademark) surfactants available from BASF-Wyandotte, Inc. Less desirably, aromatic types may also be used, such as alkylphenoxypolyethoxyethanols having alkyl groups of about 7 to 18 carbon atoms and 1 to 60 or more oxyethylene units, for example: heptylphenoxypolyethoxyethanols, octylphenoxypolyethoxyethanols, methyloctylphenoxypolyethoxyethanols, nonylphenoxypolyethoxyethanols, dodecylphenoxypolyethoxyethanols, and the like; polyethoxyethanol derivatives of methylene linked alkylphenols; sulfur-containing analogs of the foregoing; ethylene oxide derivatives of long-chain carboxylic acids, such as lauric, myristic, palmitic, oleic, and the like or mixtures of acids such as are found in tall oil containing 1 to 60 oxyethylene units per molecule; and analogous ethylene oxide condensates of long-chain or branched-chain amines, such as dodecylamine, hexadecylamine, and octadecylamine, containing 1 to 60 oxyethylene groups.

Naturally occurring emulsifiers or derivatives thereof are also useful. These include the alginates, cellulose derivatives such as methyl cellulose and carboxymethyl cellulose, water soluble gums such as gum arabic and gum tragacanth, the phospholipids (such as lecithin and yolk phospholipid), and the sterols.

Nonionic fluorine containing surfactants are particularly preferred. The fluorinated alkyl esters are one class of these surfactants, and are commercially available from 3M Company under the designations FC-93, FC-95, FC-128, FC-143, FC-430 and FC-431.

The more preferred nonionic, fluorine containing surfactants, from the standpoint of their exceptional ability to form dispersions which maintain a range of small particle size over substantial periods of time, of the order of 35 weeks to a year or more, even at room temperature, are the fluorinated amidoamine oxides described in U.S. Pat. Nos. 3,828,085 to Price et al, and 3,547,995 to Bartlett, the disclosures of which are incorporated herein by reference. These compounds may be generically described by the formula (1):

$$R_fCON-RQ \atop Y \qquad (1)$$

wherein $R_f$ is a perfluoroalkyl radical of 4 to about 25 carbon atoms or a polyfluoroalkoxyalkyl radical wherein the alkoxy group may contain 3 to about 40 carbon atoms of which at least a major portion thereof are perfluorinated and the alkyl group may contain 2 to about 40 carbon atoms, fluorinated or unfluorinated; Y is hydrogen or alkyl of 1 to 6 carbon atoms; R is an alkylene radical of the formula:

$$-C_zH_{2z}-$$

wherein z is an integer of 1 to 6; and Q is an aliphatic amine oxide radical of the formula:

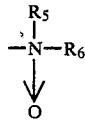

wherein $R_5$ and $R^6$ are each alkyl radicals of 1 to 6 carbon atoms or hydroxy-terminated alkyl radicals of 2 to 6 carbon atoms. In all cases the alkoxy, alkyl and alkylene groups may be straight or branched chain.

Preferred subclasses of the surfactants of the foregoing patents are those of the following formulas (2) and (3):

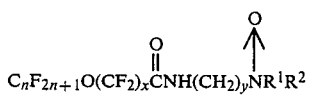

wherein n is at least 3 (preferably 3–10), x is at least 2 (preferably 2–6), y is at least 1 (preferably 2–6), and $R^1$ and $R^2$ independently are alkyl radicals containing 1–6 carbon atoms.

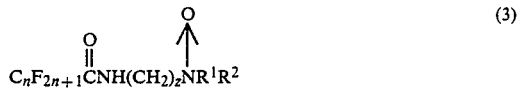

wherein n is at least 1 (preferably 3–10), z is at least 1 (preferably 2–6), and $R^1$ and $R^2$ independently are alkyl radicals containing 1–6 carbon atoms.

Specific amidoamine oxides within the scope of the above formula are the products described in Examples 1–6 of U.S. Pat. No. 3,828,085, namely:

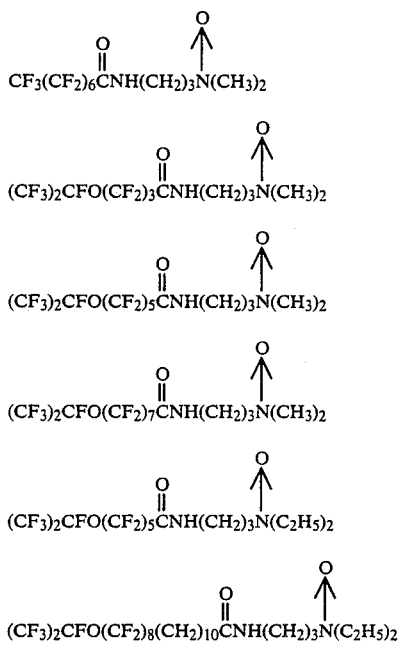

The aqueous dispersions of the invention are prepared by any mixing technique which will provide a uniform blend of the ingredients, and preparation accordingly may be readily accomplished by the skilled formulator.

When formulating the dispersions of the invention for systemic administration, it is important not only to add electrolytes and other materials to render the dispersions physiologically acceptable (such as isotonic with mammalian cells), but also to adjust the pH, as necessary, to offset the lowering of the pH of the hypoxic cell environment due to generation of lactic acid by the hypoxic tumor cells. A suitable pH range is 7.2–7.4. Among the additives commonly used to render fluids physiologically acceptable are buffers such as sodium bicarbonate, and mixtures such as Ringer's Solution. Other materials conventionally employed in pharmaceutical preparations and known to the skilled formulator may also be added to the dispersions. These include viscosity modifiers, stabilizers (against degradation due to freezing or contamination, for example), anti-freeze agents, diluents, encoding agents, and the like. Among such additives may be mentioned glycerin, dimethylsulfoxide ("DMSO"), various gelatins both natural and synthetic, and polyols such as sorbitol.

The perfluoro compound and surfactant components may be blended into water in any proportions which will provide uniform dispersions. Typical proportions are about 5 to 50% perfluoro compound based on the volume of the total composition and about 0.5 to 10% of the surfactant based on the total weight of the composition. Preferred proportions are about 10–30% by volume of the perfluoro compound and about 2–5% by weight of the surfactant, but proportions in particular cases may be varied depending on disperability of the PFC, particle size desired, and similar considerations.

The aqueous dispersions more usually comprise emulsions, preferably of the oil-in-water type but also including water-in-oil emulsions. In some cases the emulsions have a very fine particle size and appear transparent or solution-like to the unaided eye. The microemulsions which can be formulated with the dispersants of U.S. Pat. No. 3,828,085 have this characteristic and are preferred. Colloidal suspensions, while not excluded from use in this invention, are less preferred, particularly for systemic administration, because of their larger particle size range and less stability. The above-identified blood substitute and surfactant patents provide excellent guidance to formulation of the dispersions, and attention is directed to the patents for such purpose.

Sensitizing Treatment

The aqueous dispersions containing the oxygen transporting perfluoro compound, when used as sensitizers in accordance with the invention, may be administered to a mammal locally or in any systemic fashion, whether intravenous, subcutaneous, intramuscular, parenteral, intraperitoneal or oral. Preferably, administration will be systemic and at a site enabling the dispersion to traverse the lungs to pick up oxygen and to transport the oxygen to the hypoxic tumor cells. Dosages of the dispersion will be predetermined in accordance with the site and character of the hypoxia, whether or not the treatment is a supplement to hyperbaric oxygen treatment, the systemic tolerance (toxicity) of the mammal to the specific formulation, and other factors known to the therapist. Generally, fluorocrits (cc of PFC per 100 ml blood) of the perfluoro compound should be in the range of about 3–10%, although lower or higher fluorocrits in special circumstances may be sufficient or required. If the administration is a supplement to hyperbaric oxygen treatment, or other form of primary oxygen infusion, the fluorcrit need not be over 3.5%, and the partial pressure of oxygen in the inspired air may be up to about 2 atmospheres at 100% oxygen. As a maximum in most cases, hyperbaric oxygen administration would be 30 minutes at 2 atmospheres 100% oxygen pressure, and these conditions are known to be well within tolerated levels. However, the duration, content and pressure of the primary oxygenation in specific cases again will depend upon various factors, such as the health of the mammal or patient, the site of the hypoxia, and other conditions familiar to the radio- or chemotherapist.

Contact of the PFC dispersion may be with the hypoxic cells or with the tumor cell vasculature, such that the oxygen carried by the PFC may transfer to the tumor/vasculature interface. In other words, while the ideal may be direct contact between the PFC dispersion and the hypoxic cells, this may not be achievable and in fact is not required, since excess oxygen, wherever present in the tumor mass, will tend to become distributed throughout the mass, and thus reach the hypoxic cells.

The dosage of the sensitizing agent prior to irradiation and/or chemotherapy will also be controlled by various conditions, including the rate at which the perfluoro compound travels to the hypoxic tumor cells, the degree of sensitization desired, and the cardiovascular half-life residence time of the dispersion in the cardiovascular system and in the hypoxic tissues. For some treatments (such as brief radiation treatments) an acceptable cardiovascular (serum) half-life can be as brief as about 2 to 4 hours. This duration indicates that the perfluoro compound moves rapidly to the hypoxic tumor cells and transfers its oxygen to the cells. In this connection an outstanding property of the preferred dispersions of the invention is an extremely small particle size, which particle size is maintained over substantial periods. The small particle size enables the dispersions to quickly traverse the vasculature to the site of the hypoxia. For example, an average particle size of 0.05 to 0.2 micron has been observed and has been maintained for several months and up to a year or more.

The dispersions may be oxygenated prior to infusion into the mammalian body and this may be expedient when injection is at or near the site of the hypoxia rather than at a site where oxygen transfer from the lungs and arteries is anticipated. Prior oxygenation in such manner may be accomplished by any means, such as flushing or blanketing a vessel containing the dispersion with oxygen or air, or bubbling oxygen or air through the dispersion prior to administration. When the treatment is a supplement to hyperbaric oxygen treatment, preoxygenation in the manner described may also be practiced. In every case of preoxygenation, however, there may be a loss of oxygen prior to entry of the dispersion into the region of the hypoxic tumor cells, that is, during transit of the dispersion to the cells; hence, preoxygenation generally is not preferred.

The types, mode of application and sites of radiation treatments are well known and do not require detailed description. However, it will be evident that irradiation can be accomplished by external application or by internal placement of radiation sources near or at the site of the hypoxia. Accordingly, the irradiation may be achieved with x-rays, gamma rays, neutrons and the like, or with implanted radium, iridium or cesium sources. Conventional radiation therapy (200 rads per day, five days per week for six to eight weeks) may be employed but dosage and total duration of treatment may be adjusted as required in particular circumstances.

The sensitizing method of the invention will be effective for all types of hypoxic tumor cells, whether such cells be in suspension (as in leukemia) or in solid form, but the invention is particularly effective for solid tumors. Because systemic distribution of the dispersions is rapid, primarily due to the extremely small and stable particle size of the preferred dispersions of the invention, hypoxia at practically any site may be sensitized in accordance with the invention.

Chemotherapy is often used in combination with radiotherapy to destroy or control hypoxic tumor cells and therefore the sensitization techniques of the invention can be applied simultaneously or sequentially to chemotherapy and radiotherapy. When dual therapy is used, a sensitizer dispersion will normally be selected which has the cardiovascular residence time effective to cover the duration of both treatments, or if the residence time is short, the sensitizer dosage can be suitably increased or adjusted. It is known that some chemotherapeutic agents are oxygen dependent in terms of requiring oxygen for active transport of the CT drug into the cell, for cell cycling control or CT enhancement. Hence, oxygen must be supplied in free form or by means of a carrier. Because the perfluoro compounds of the present invention and their dispersions are capable of transferring large quantities of oxygen, it can be expected that chemotherapy based upon drugs which are oxygen dependent will be benefited by formulating the drugs with an RS agent of the present invention, or sequentially administering the RS and CT agents. Methotrexate is an example of a CT drug thought to require oxygen for active transport into the cell. Vinblastine and Vincristine are drugs which require oxygen for cell cycling.

CT drugs which may not be oxygen dependent may also be administered in conjunction with the sensitizing techniques of the invention. Among such drugs may be mentioned Androgens, Estrogens, Anti-estrogen, Progestins, Adrenal Steroids, Nitrogen Mustard, Chlorambucil, Phenylalanine Mustard, Cyclophosphamide, Thio-TEPA, Busulfan, 6-Mercaptopurine, 6-Thioguanine, 5-Fluorouracil, Cytosine Arabinoside, Adriamycin, Dactinomycin, Daunomycin, Bleomycin, Mithramycin, Mitomycin-C, BCNU, CCNU, Methyl-CCNU, DTIC, Hydroxyurea, Cis-Platinum (cis-platinum (II) diamminedichloride), Procarbazine, Hexamethylmelamine, L-Asparaginase, and the like.

Associated Treatments

Those perfluoro compounds useful as RS agents but which also have radiopaque properties are particularly valuable for the purposes of the present invention. Such compounds include brominated perfluorohydrocarbons such as F-perfluoroctylbromide and brominated perfluoroethers, such as F-1-bromobutylisopropylether, F-1-bromoethylisopropyl ether and other brominated perfluoro organo ethers described, for example, in U.S. Pat. No. 3,453,333. The radioimaging properties of such compounds permit monitoring of their RS effects as well as toxicity to surrounding normal cells and hence serve as diagnostic agents as well as RS agents. However, if the perfluoro compounds do not also exhibit radiopacity, the dispersions containing the perfluoro compounds may be formulated with other, known, radiopaque agents in order to provide a similar opportunity for monitoring radiosensitization potential. The radioimaging may be practiced as in conventional radiography or computer axial tomography (CAT) radiography, or by the newer NMR techniques. The brominated compounds as RI agents may be used neat or in aqueous dispersion, for example as oil-in-water or water-in-oil emulsions containing about 10–90% by volume of water and about 0.5–10% by weight of a dispersant.

Radioprotection may also be practiced in conjunction with the radiosensitization of the invention. Radioprotective agents are those which preferentially protect normal tissues from radiation injury. When practiced with radiosensitization, the objective is to reduce injury to the normal tissues, which injury may occur when the RS agents are used in the absence of the RP agents. Sulfhydryl-containing agents generally are known to be effective RP materials, such as aminoethylisothiuronium or the phosphorothioate derivatives of beta-mercaptoethylamine reviewed in the article by J. M. Yuhas, "On the Potential Application of Radioprotective Drugs in Solid Tumor Radiotherapy," appearing in Radiation-Drug Interactions in the Treatment of Cancer, edited by G. H. Sokol and R. P. Maickel, John Wylie and Sons, Inc. (1980), pages 113–135. Another RP agent is S-2-(3-aminopropylamino)ethylphosphorothioic acid, also described in the literature as WR-2721. This material provides protection both in radiotherapy and chemotherapy, as described in the article by Yuhas et al appearing in Cancer Clinical Trials (1980), 3, 211–216.

The following examples will serve as further illustration of the invention without necessarily limiting the scope thereof. While the experimental results of Examples 2, 4 and 7 were obtained in vitro, the sensitization demonstrated by these examples is not restricted to non-mammalian systems because the MTS studies are known to correlate with patterns of the response of the cells in mammals. Specifically, the MTS are known to respond similarly to the same tumor when grown in the mammalian body.

EXAMPLE 1

Preparation of PFC dispersions:

(A) A surfactant solution was prepared by dispersing in water a sufficient amount of the following amidoamine oxide surfactant ("AAO") to provide a 2% by weight solution:

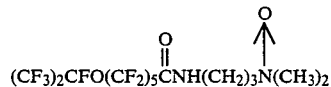

to the sonication chamber of a "Sonicator" (trademark) mixing device (Heat-Systems Ultrasonics, Inc., Model 350) was added 27 cc of the 2% surfactant solution, followed by slow addition (over 3–4 minutes) under low sonication power of 3 cc (to give 20 wt.% or 10 vol. %) of a PFC composition consisting of an about 80/20 by weight liquid mixture of F-1,3-dimethyladamantane and F-trimethylbicyclo[3.3.1]nonane, to provide a total of 30 cc of composition. (The PFC mixture was previously saturated with $CO_2$ to inhibit formation of fluoride ions.) The sonication horn was then turned up to full power (setting of 10 on a scale of 1–10) for one minute followed by a cooling period. This cycle was repeated about 15 times or until such time as a transparent, uniform dispersion was obtained. The dispersion (hereinafter identified as "Dispersion A") was then filtered through a 0.22 micron "Millipore" (trademark) filter and kept refrigerated at 4° C. until use.

(B) A second dispersion was prepared substantially as in (A) above except for use of a nonionic polyoxyethylene—polyoxypropylene copolymer surfactant having a molecular weight of about 8200 ("Pluronic" F-68) in place of the AAO surfactant. This dispersion is hereinafter identified as "Dispersion B."

(C) A third dispersion was prepared substantially as described in (A) above except that the PFC was F-tributylamine (FC-43," 3M Company) and the surfactant was the "Pluronic F-68" of (B). The proportions were the same (10 vol.% PFC, 2 wt.% surfactant). This dispersion is hereinafter identified as "Dispersion C."

EXAMPLE 2

In Vitro Radiosensitization

Multicellular tumor spheroids ("MTS") are produced by placing $10^6$ MCa-11 murine mammary tumor cell in 10 mls of Eagles Basal Medium ("EBME"), Grand Island Biological Co., catalog No. 420-1200, into a 100 mm petri dish which has been base coated with 0.75% noble agar in the EBME. Within 7-10 days spherical aggregates of tumor cells appear and are then ready for study. The PFC dispersion to be tested is adjusted to 290 milliosmoles osmolarity with powdered tissue culture medium and adjusted to pH 7.2 to 7.4 with 0.1N NaOH or HCl. Other details of preparation and use of the MTS are given in J. M. Yuhas et al, 1977, "A Simplified Method For Production And Growth Of Multicellular Tumor Spheroids," *Cancer Research* 37:3639-3643; and J. M. Yuhas et al, 1978, "In Vitro Analysis Of The Response Of Multicellular Tumor Spheroids Exposed to Chemotherapeutic Agents In Vitro Or In Vivo," *Cancer Research* 38:3595-3598.

Either standard tissue culture medium (EBME) or the PFC dispersion is gassed with 100% oxygen for a period of fifteen minutes and then transferred, along with the spheroids, into non-heparinized capillary tubes and sealed. At intervals of 0 to 60 minutes later the tubes are exposed to graded doses of 250 kVp X-rays, and within 30 minutes thereafter are removed, washed with medium and placed individually in agar coated 16 mm wells along with 1.5 cc of medium. Using a dissecting scope at 40 power the spheroids are sized three times weekly and the medium is changed twice weekly. From the growth curves for each group is calculated the number of days required for each spheroid to grow 200 or 150 μm (microns) in diameter larger than the size at the beginning of the irradiation. The retardation of rate of growth of the spheroids shown by the data therefore provides a measure of RS response where the larger the difference over the irradiated controls the greater the RS effect. Toxicity of the PFC is evaluated in terms of growth delay, i.e., the retardation in growth of the spheroids after exposure to the PFC (without irradiation) relative to that observed in untreated spheroids. Table I below shows the results of experiments with Dispersions A and B and Table II shows results with Dispersion C.

It will be noted that Dispersions A and B provided similar levels of toxicity and radiosensitivity. The toxicity exhibited by Dispersions A and B is considered negligible and likely to be relatively tolerable in the cardiovascular system. The toxicity exhibited by Dispersion C, although higher than that of Dispersions A and B, does not disqualify Dispersion C from use as a sensitizer in mammals; such toxicity is relative to various factors, such as RS reagent and radiation dosage, and tumor type and location, and therefore Dispersion C would not necessarily be excluded from clinical evaluation. The data of Tables I and II is not directly comparable; larger spheroids were used in the experiments reported in Table I than were used in the experiments reported in Table II. However, the larger spheroids provide added bias (larger spheroids are more difficult to sensitize) and therefore the results of Table I indicate highly beneficial sensitization.

On face value, it would appear that Dispersion C is a more effective radiosensitizer than either Dispersion A or Dispersion B. This is in all probability not true for two reasons. The studies with Dispersion C were preliminary and involved MTS with a smaller fraction of radioresistant hypoxic cells at the time of treatment than was the case for the studies with Dispersions A and B. Second, Dispersion C was, in itself, growth inhibitory, and it is likely that this property in some way enhanced the tumor cell destruction.

TABLE I

| System | Radiation (rads) | Days to Grow 200 um | Toxicity | Growth Delay (Days) Radiation Effect | RS Effect |
|---|---|---|---|---|---|
| MTS/EBME | 0 | 4.1 | $0^a$ | — | — |
| MTS/EBME | 750 | 5.3 | $0^b$ | $1.2^c$ | — |
| MTS/EBME/ Dispersion A | 0 | 4.4 | $0.3^d$ | — | — |
| MTS/EBME/ Dispersion A | 750 | 9.0 | $0.3^b$ | $4.6^c$ | 3.7 |
| MTS/EBME/ Dispersion B | 0 | 4.1 | $0^d$ | — | — |
| MTS/EBME/ Dispersion B | 750 | 8.9 | $0^b$ | $4.8^c$ | 3.6 |

TABLE II

| System | Radiation (rads) | Days to Grow 150 um | Toxicity | Growth Delay (Days) Radiation Effect | RS Effect |
|---|---|---|---|---|---|
| MTS/EBME | 0 | 3.8 | $0^a$ | — | — |
| MTS/EBME | 750 | 11.5 | $0^b$ | $7.7^c$ | — |
| MTS/EBME/ Dispersion C | 0 | 8.4 | $4.6^d$ | — | — |
| MTS/EBME/ Dispersion C | 750 | 30 | $4.6^b$ | $21.6^c$ | 18.5 |

$^a$By definition.
$^b$Assumed to be same as unirradiated control.
$^c$Observed time minus time required by respective unirradiated group.
$^d$Observed time minus time required by unirradiated control group.

EXAMPLE 3

In Vivo Studies (Residence Times)

The rate of clearance of PFC dispersions A and B from the circulation was evaluated in both Fisher 344 rats and BALB/c mice (females in both cases). The dispersion were injected intravenously to a PFC dose equal to one-third of the circulatory volume, which is equal to 6% of body weight. Within 30 minutes of injection, the animal returns to the normovolemic state as evidenced by the fact that the fluorocrit equals 3.1% compared to the theoretical estimate of 3.3% for these Dispersions. At graded intervals through 8 hours after injection, blood is drawn in microcapillary tubes from the supraorbital sinus. Following centrifugation for 15 minutes at 12,000 times gravity, the fluorocrit (PFC as a percent of the blood volume) and the hematocrit are read on a microscope. The PFC collects as a pellet in the bottom of the tubes, followed by the red blood cells and the plasma, thus forming distinct layers. All data are normalized to the 30 minute centrifugation reading and the rate of decline of the fluorocrit is estimated from a standard single compartment exponential decay curve defined by:

$$\% \ PFC \ \text{remaining} = e^{-kt}$$

and $$T_{\frac{1}{2}} = \frac{\ln 2}{k}$$

The results when plotted show that Dispersion A is superior to Dispersion B (half lives of 366 minutes and 222 minutes, respectively), probably because Dispersion A has a smaller particle size than Dispersion B. The results for the rats and mice were essentially equivalent. The results indicate that the PFC in both dispersions will clear the cardiovascular system quickly, and therefore both dispersions are good candidates for clinical studies.

EXAMPLE 4

The MTS experiments of Example 2 were repeated in all essential respects with Dispersion B but using spheroids derived from human tumor lines which contain hypoxic cells when grown as MTS. As shown in Table III below, some toxicity was observed in all cases but the levels are considered relatively tolerable. Moderate radiosensitizing is apparent for the two neuroblastoma cell lines but very high radiosensitization is shown with respect to the melanoma line. The latter is an outstanding result due to the prevalence and high risks known for this form of hypoxic tumor cells. Very little RS effect is shown for the osteosarcoma cell line but these results are only preliminary and the exposure was at a low radiation level.

curred at the high doses probably were due to fluid overload rather inherent toxicity of the PFC dispersions.

TABLE IV
ACUTE TOXICITY OF DISPERSION B
ADMINISTERED HYPERVOLEMICALLY I.V. IN RATS

| DOSE (ml/kg) | NUMBER DEAD ÷ NUMBER INJECTED |
|---|---|
| 20 | 0/11 |
| 40 | 0/3 |
| 60 | 0/3 |
| 80 | 0/3 |
| 100 | 0/2[a] |
| 120 | 1/3 |

[a]One animal died during injection due to mishandling.

EXAMPLE 6

In Vivo Radiosensitization

Radiosensitization of the 3M2N mammary tumor growing in the right hind leg of Fisher −344 rats was

TABLE III

| Human Tumor Line | System | Radiation (rads) | Days to Grow 200 um | Growth Delay (Days) Toxicity | Growth Delay (Days) Radiation effect | RS Effect |
|---|---|---|---|---|---|---|
| NB-100 Neuroblastoma | EBME/MTS | 0 | 6.5 | 0 | — | — |
| | EBME/MTS | 400 | 7.4 | 0 | 0.9 | — |
| | EBME/MTS/Dis. B | 0 | 6.6 | 0.1 | — | — |
| | EBME/MTS/Dis. B | 400 | 10.0 | 0.1 | 3.4 | 2.6 |
| LAN-1 Neuroblastoma | EBME/MTS | 0 | 4.9 | 0 | — | — |
| | EBME/MTS | 400 | 5.2 | 0 | 0.3 | — |
| | EBME/MTS/Dis. B | 0 | 5.2 | 0.3 | — | — |
| | EBME/MTS/Dis. B | 400 | 9.3 | 0.3 | 4.1 | 4.1 |
| SAOS Osteosarcoma | EBME/MTS | 0 | 8.6 | 0 | — | — |
| | EBME/MTS | 250 | 12.9 | 0 | 4.3 | — |
| | EBME/MTS/Dis. B | 0 | 10.7 | 2.1 | — | — |
| | EBME/MTS/Dis. B | 250 | 14.0 | 2.1 | 3.3 | 1.1 |
| C-32 Melanoma | EBME/MTS | 0 | 7.9 | 0 | — | — |
| | EBME/MTS | 750 | 10.5 | 0 | 2.6 | — |
| | EBME/MTS/Dis. B | 0 | 8.4 | 0.5 | — | — |
| | EBME/MTS/Dis. B | 750 | 17.4 | 0.5 | 9.0 | 6.9 |

EXAMPLE 5

Acute Toxicity

Studies were undertaken to confirm suitability of PFC emulsions for intravascular administration and oxygen transport. The emulsion tested was Dispersion B which was held at 4° C. until use. Just prior to use the osmolarity was adjusted to approximately 300 milliosmoles with powdered tissue culture medium (Eagles Basal Medium—"EBME"), and the pH adjusted to 7.4 with HCl or NaOH. Table IV below summarizes the results of an acute toxicity study on Fisher −344 rats in which various doses of the emulsion were injected into the tail veins of the rats. Rats reported as surviving after injection survived for at least ten days. Deaths normally occurred in 4 to 24 hours if at all. The results indicate that the animals can tolerate large doses of PFC emulsion relative to their blood volume (about 60 to 80 ml/kg) as compared with the doses which would be administered to assess radiosensitization in vivo, namely, 20 to 30 ml/kg. In $LD_{50}$ (I.V.) tests it was determined that the lethal dosage was greater than 60 ml/kg for BALB/c mice and greater than 120 ml/kg for the Fisher −344 rats. The observations are consistent with those reported by other investigators in that the PFC dispersion has a low acute toxicity even when administered hypervolemeically at doses exceeding the animal's normal blood volume. The deaths which ocstudied. At 10–14 days after subcutaneous transplantation in the rats the tumors were 6–8 mm in diameter and ready for treatment. The control animals either received no treatment or received various radiation doses. The other animals received I.V. infusion of 20 ml/kg of Dispersion B (20% w/v) followed by 30 minutes breathing of 95% $O_2$/5% $CO_2$ gas mixture (at 1 atm) and then by the various radiation doses of x-rays. Prior to and three times weekly after treatment, the two orthogonal diameters of the tumors were measured in situ and averaged. Table V below expresses the results of the study as the time required for the tumors to grow 8 mm beyond their size at the time of treatment. The data show that the enhancement produced by the PFC dispersion increases with radiation dose, and also that the growth delay per rat is significantly higher in the PFC-treated group than in the control. That the enhancement is due to the combination of the PFC dispersion and breathing of the gas mixture is evident from Table VI below in that none of the control treatments were capable of producing the growth delay of the combination.

TABLE V

RADIOSENSITIZATION OF 3M2N TUMORS IN RATS AT DIFFERENT RADIATION DOSES WITH DISPERSION B

| RADIATION DOSE (RADS) | DAYS TO GROW TO 8 mm | |
|---|---|---|
| | CONTROLS | DISPERSION B PLUS HIGH OXYGEN |
| 0 | 11.5 ± 0.8 | 11.5 ± 1.1 |
| 500 | 10.9 ± 0.9 | 12.0 ± 0.9 |
| 1500 | 19.5 ± 0.9 | 24.9 ± 0.8 |
| 2500 | 25.2 ± 1.4 | 35.7 ± 1.3 |

TABLE VI

EFFECTS OF VARIOUS CONTROL TREATMENTS ON GROWTH OF 3M2N TUMORS IN RATS

| | | |
|---|---|---|
| None | 12.3 ± 1.4 | — |
| Emulsion[a] | 12.9 ± 0.9 | 0.6 |
| 2,500 Rads | 27.3 ± 2.4 | 15.0 |
| Saline[a] + 2,500 Rads | 25.3 ± 3.1 | 13.0 |
| Emulsion[a] + 2,500 Rads | 24.4 ± 2.8 | 12.1 |
| 95% $O_2$/5% $CO_2$ + 2,500 Rads | 29.8 ± 3.1 | 17.5 |

[a]20 ml/kg of Dispersion B or equal volume dose of saline.

EXAMPLE 7

In Vitro Chemosensitization

The potentiation by PFC dispersions of chemotherapeutic agents was demonstrated by the anti-tumor effect of methotrexate ("MTX") in NB-100 neuroblastoma multicellular tumor spheroids ("MTS"). In this study, the speroids were exposed to from 0 to $5 \times 10^{-6}$ molar methotrexate in control medium and in Dispersion B equilibrated with a 95% $O_2$/5% $CO_2$ mixture. The results (Table VII below) show that the PFC dispersion enhanced the effectiveness of MTX as evidenced by the delay in growth relative to the spheroids treated only with MTX. Although some sensitization to MTX in these spheroids can be achieved by gassing with the gas mixture in medium alone, such sensitization requires 1 to 2 hour pretreatment as opposed to only 30 minutes with the PFC dispersion, thus clearly demonstrating the feasibility of elevating the therapautic index of this important anti-cancer drug with PFC.

TABLE VII

Effects of PFC Dispersion B and oxygen on the response of NB-100 MTS to a 24 hour exposure to 5 uM MTX for 24 hours.

| | CONTROLS | MTX | PFC DISPERSION + MTX |
|---|---|---|---|
| Day 0 | 9.17 ± 0.31[a] | 9.83 ± 0.17 | 9.90 ± 0.23 |
| 1 | 10.23 | 9.74 | 9.77 |
| 4 | 13.78 | 10.69 | 9.66 |
| 6 | 15.72 | 11.76 | 9.83 |
| 8 | 17.17 | 13.93 | 10.90 |
| 12 | | 18.93 | 15.81 |
| 15 | | 21.83 | 19.0 |
| 18 | | | 23.5 |
| D8[b] | 7.18 | 9.52 | 13.02 |

[a]MTS sizes are given in microscope units, where 1 unit = 25 um
[b]D8 is the number of days required for the MTS to grow 8 units or 200 um beyond their original diameter.

EXAMPLE 8

In Vivo Chemosensitization

The combined use of PFC dispersion (Dispersion B) and high oxygen breathing for enhancement of the anti-tumor effects of cyclophosphamide ("CYC") was investigated with respect to treatment of MCa-11 mammary carcinoma transplanted into the right hind leg of female BALB/c mice. The tumors were allowed to grow to 2 mm at which point the animals were treated as described in Table VIII below, wherein the cyclophosphamide, obtained commercially, was dissolved in distilled water and injected in a volume equal to 0.01 ml/kg of body weight. Three to six animals per treatment group were used in the study. On the day of treatment and three to five times per week thereafter, the tumors were sized with vernier calipers.

From the test results (Table VIII), it is evident that the anti-tumor effect (growth delay) produced by the cyclophosphamide alone (absence of oxygen and/or PFC dispersion) was not detectably enhanced by oxygen breathing (of 95% $O_2$/5% $CO_2$ mixture) or by injection of PFC dispersion followed by oxygen breathing, but was enhanced effectively by administration of PFC dispersion in concert with oxygen breathing.

TABLE VIII

Effects of PFC ± Oxygen on the Antitumor Effectiveness of Cyclophosphamide

| Treatment[a] | Number of Mice | Days to Grow 6 mm.[b] | Growth Delay |
|---|---|---|---|
| Controls | 14 | 12.5 | — |
| Cyclophosphamide | 5 | 17.8 | 5.3 |
| PFC + CYC | 4 | 17.1 | 4.5 |
| Oxygen + CYC | 5 | 16.6 | 4.1 |
| PFC + Oxy. + CYC | 6 | 20.8 | 8.3 |

[a]Controls = no treatment; Cyclophosphamide = given a single dose of 75 mg/kg of cyclophosphamide via i.p. injection; PFC = given a single injection of 20 ml/kg of F-DMA/F-NONAN 2 hours before receipt of the cyclophosphamide; and Oxygen = maintained in an atmosphere of 95% oxygen + 5% $CO_2$ for 2 hours before and two hours after administration of the cyclophosphamide. In the combined PFC + oxygen group, the PFC was administered just before the mice were placed in the 95% oxygen atmosphere.
[b]the days required to grow 6 mm were interpolated from the tumor growth curves constructed from the test data.

EXAMPLE 9

In Vivo Chemoprotection and Chemosensitization

Combined chemosensitization of hypoxic tumors to chemotherapeutic agents and protection of normal tissues is achieved by the procedure described by Yuhas et al, "Treatment of Tumours with the Combination of WR-2721 and Cis-dichlorodiammine platinum (II) or Cyclophosphamide," Br. J. Cancer (1980), 42, 574–585 and publications referenced therein, as modified by concurrent treatment with 20 ml/kg of a PFC dispersion, such as Dispersion B, as described in Example 8 above, to accommodate lower dosages of the chemotherapeutic agents (75 mg/kg), room air breathing, high oxygen (95% $O_2$/5% $CO_2$) breathing, controls, and other conditions as appropriate.

EXAMPLE 10

In Vivo Radioprotection and Radiosensitization

The sensitization of hypoxic tumors to irradiation by treatment with PFC compositions of the invention in combination with radioprotection of normal tissues in the region of treatment is achieved by the procedure described by Yuhas et.al, "The Role of WR-2721 In Radiotherapy and/or Chemotherapy," Cancer Clinical Trials (1980), 3, 211–216 and publications referenced therein, modified as described in Example 6 above to provide for concurrent infusion of 20 ml/kg of a PFC composition such as Dispersion B, high oxygen (95%

$O_2/5\%$ $CO_2$) or air breathing, controls, and other conditions as appropriate.

Delivery of Lipophilic Drugs

In the course of in vitro chemosensitization studies in the LAN-1 human neuroblastoma spheroid system, conducted substantially as described in Example 4 above except for Adriamycin as the chemotherapeutic agent, it was noted that the anti-tumor activity of the Adriamycin was inhibited by the PFC material (PFC Dispersion B). This suggested that the PFC may have been physically binding the Adriamycin, thereby reducing the concentration available for absorption by the spheroids. This was tested by dissolving in water a radio-labelled analogue of Adriamycin, $C^{14}$-Daunomycin, adding Dispersion B (or in separate experiments, the neat PFC component of Dispersion B), blending for 30 minutes, separating the PFC phase from the aqueous phase, and determining the distribution of drug between the phases. Table IX below reports the results of the experiment similar experiments with three other drugs. It will be noted that the more lipophilic Daunomycin preferentially partitioned into the PFC phase whereas the other, less lipophilic, drugs favored the aqueous phase. It was concluded that although the PFC may have an inhibitory effect on less lipophilic drugs, the delivery of lipophilic drugs will be enhanced by the PFC.

TABLE IX
BINDING OF FOUR CANCER TREATMENT DRUGS BY PFC DISPERSION

| Drug | Lipophilicity Index* | Drug in Emulsion ÷ Drug in Aqueous Phase |
|---|---|---|
| Daunomycin | 0.79 | 3.77 |
| Misonidazole | 0.43 | 0.04 |
| Methotrexate | 0.014 | 0.07 |
| WR-2721 | 0.002 | 0.05 |

*Lipophilicity index is the partition coefficient of the drug between octanol and water.

The preferential solubility of lipophilic drugs in PFC compositions not only provides a means for enhancing the delivery of such drugs in animals but also opens up opportunity for controlling residence time of the drug in the animal, for example by prolonging release of the drug from PFC circulating to the plasma and target organs. In other words, by appropriate selection of a drug from the standpoint of its relative lipophilicity in a PFC dispersion, sustained low level delivery of a drug for a prolonged period is made possible with an aqueous delivery system.

EXAMPLE 11

Enhancement of Chemotherapy

This example illustrates enhancement of anti-tumor action of Vincristine, a lipophilic drug to which tumors are normally resistant at least to non-lethal doses thereof. The enhancement is believed due to the preferential solubility of the drug in the PFC material.

The partitioning of the Vincristine between the PFC and aqueous phases of Dispersion B was first studied in comparison with Daunomycin, as reported in Table X below, where "PFC" means the PFC phase of Dispersion B.

TABLE X

| Drug | Octanol:Water Partition Coefficient[a] | PFC/$H_2O$[b] 1 hour | 3 hours |
|---|---|---|---|
| Daunomycin | 0.79 | 1.23 | 3.80 |
| Vincristine | 682 | 2.69 | 9.10[c] |

[a]The higher the octanol:water partition coefficient, the more lipophilic is the drug.
[b]ratio of concentrations in the emulsion and the aqueous phases.
[c]determined via bioassay in the LAN-1 neuroblastoma spheroid system.

Thereafter, in vivo chemosensitization was conducted in MCa-11 mammary carcinoma essentially as described in Example 8 above except as follows:

The MCa-11 mammary carcinoma was transplanted into the thigh of BALB/c mice and grown to a diameter of 6 mm, at which time the mice were treated. Control mice received an injection of saline, while Vincristine treatment consisted of a single dose of 1.5 mg/kg of Vincristine administered intraperitoneally. PFC treatment consisted of an i.v. injection of 20 ml/kg of Dispersion B, followed by two hours of breathing carbogen (95% $O_2$/5% $CO_2$), and injection of saline or Vincristine as before, followed by another two hours of carbogen breathing. It was observed that the Vincristine treatment alone had no effect on tumor growth. Similarly, administration of the PFC emulsion alone had no effects on tumor growth, but when combined with the injection of Vincristine, the growth of the tumor was delayed by approximately 5 days. Oxygen breathing was included in the experiment in order to guarantee that any stimulation of the active efflux mechanism might not override any potential benefits gained via a more advantageous delivery of drug. In vitro studies now underway indicate that the benefits of the PFC-Vincristine combination are not oxygen dependent. Moreover, enhanced host toxicity of the Vincristine when combined with the PFC dispersion could not be detected. Thus, it appears that PFC dispersion have the potential to deliver low levels of drugs over prolonged periods.

It will also be apparent that by matching PFC materials and drugs based on their relative lipophilicity and the rate of clearance of PFC material from the body, the efficacy of drugs in a variety of treatments may be controlled. In some cases the effect may be enhancement of activity. In other cases diminished activity or prolonged activity may be the preferred result. The latter effect is obtainable, for example, selection of a PFC carrier material which is known to clear more slowly from the body than will another PFC material. These benefits are achievable whether or not the PFC material is also being utilized as an oxygen transporting agent.

There are a number of instances in which the solubility of drugs in PFC could be exploited in medicine. If, as in the cases mentioned above, one selects a highly lipophilic drug which preferentially partitions into the organic, PFC phase, it is possible to produce a sustained drug delivery system. As the tissues absorb the drug from the aqueous phase, a new equilibrium will be established, i.e., some of the drug in the organic phase will transfer back into the aqueous phase. In practice, this would be a continuous process, which provides chronic, low level drug exposure. Three general classes of drugs can be envisoned: those which are totally insoluble in PFC (very hydrophilic), those which are of similar solubility in the PFC and water, and those which are more soluble in the PFC (very lipophilic). While lipophilicity is not the sole determinant of solubility in the two phases, it is a major determinant and can be used as a guide in the selection of candidate drugs.

One additional characteristic must be considered, the "loading factor"; this is the absolute solubility of the drug in the PFC. The emulsion must be able to carry a therapeutic dose level, i.e., not become saturated at less than desirable concentrations.

Specific applications of this approach include, but are not limited to: (1) chronic administration of lipophilic, phase specific cancer chemotherapeutics, such as Vincristine sulfate; (2) chronic administration of lipophilic cardiovascular agents, such as Digitoxin; (3) chronic administration of lipophilic nutritional supplements like Vitamin E; (4) chronic administration of lipophilic hormones, such as Estradiol; and (5) chronic administration of any lipophilic agent whose effectiveness would be enhanced or whose toxicity would be reduced via chronic administration.

In those instances where water solubility is too low for effective dispersion in a PFC emulsion, the drug can be introduced directly into the PFC, followed by dispersion of the PFC in water.

Useful guidance to drug absorption is present in "Prediction Of The Volume Of Distribution From In Vitro Data An Use For Estimating The Absolute Extent Of Absorption", W. A. Ritschel and G. V. Hammer, International Journal of Clinical Pharmacology, Therapy and Toxicology, 18: 298–316 (No. 7, 1980). This article (incorporated herein by reference) defines Apparent Distribution Coefficient (APC) in a buffered octanol/water mixture as follows:

$$APC = \frac{(C°_a - C'_a) \cdot a}{C_a \cdot b}$$

where $C°_a$ is drug concentration in the aqueous phase before equilibrium, $C'_a$ is drug concentration in aqueous phase after equilibrium, a is volume of aqueous phase, and b is volume of the octanol phase. The mixture is at equilibrium when the concentrations of drug in the octanol and aqueous phases remain constant at a given temperature after suitable agitation. In the system used to determine APCs in the Ritschel and Hammer article, equilibrium was reached after 8 hours agitation at 37° C. APC as defined above is useful in selecting drugs whose therapeutic efficacy can be enhanced pursuant to the present invention.

Preferably the drug is one having an APC (in a 50/50 by volume equilibrium mixture of water and the perfluorocarbon compound or mixture of perfluorocarbon compounds) reflecting a level of absorption into the PFC phase effective for therapeutic blood levels, such as at least 1.0, more preferably over 1.0. Equilibrium will be the point of admixture at which the concentration of drug in each of the two phases is constant at 37° C. Buffering of the PFC dispersion is optional.

The foregoing describes some aspects of lipophilic drug manipulation for improved delivery and therapeutic effect. It will be apparent that by matching PFC compounds and drugs on the basis of their relative lipophilicity in aqueous media, it is now possible to determine the amount of a specific drug to be added to a perfluorocarbon dispersion in order to deliver a concentration of the drug in the blood in a therapeutic range (therapeutic concentration ranges are known for all approved drugs), since knowing the lipophilicity of the drug in the PFC dispersion by APC measurement, one has guidance to prediction of how much of the drug will be available for therapeutic effect and the rate at which the drug will be made available. A wide spectrum of therapeutic effect is, of course, represented by the great variety of lipophilic drugs available as indicated, for example, in the current edition of The Merck Index and similar compilations. The drugs thus include many chemotherapeutic agents, chemotherapeutic protective agents and radioprotective agents such as those identified herein, as well as the drugs of the Ritschel and Hammer article cited above. The invention thus opens up vast opportunity for enhanced therapy over a wide spectrum of medical treatments.

The invention claimed is:

1. A method of delivering a lipophilic drug in an animal, comprising administering to the animal a therapeutically effective amount of the drug in an aqueous dispersion of a perfluoro compound capable of carrying oxygen.

2. The method of claim 1 wherein the drug is Daunomycin.

3. The method of claim 1 wherein the drug in Vincristine.

4. The method of claim 1 wherein the aqueous dispersion contains a dispersant for the perfluoro compound and the perfluoro compound comprises a mixture of F-trimethylbicyclo[3.3.1]nonane and F-dimethyladamantane.

5. An aqueous pharmaceutical composition comprising an emulsified perfluorocarbon capable of carrying oxygen and a therapeutically effective amount of an additive selected from a lipophilic drug, a chemotherapeutic agent, a chemotherapeutic protective agent, a radioprotective agent, and a mixture of two or more thereof.

6. The composition according to claim 5 wherein said perfluorocarbon is perfluorinated cyclic hydrocarbon.

7. The composition of claim 6 wherein said perfluorinated cyclic hydrocarbon is non-aromatizable, polycyclic and contains at least two bridgehead carbon atoms linked through a bridge containing at least one carbon atom.

8. The composition of claim 5 wherein the average particle size of the emulsified perfluorocarbon is in the range of 0.05 to 0.2 microns.

9. The composition of claim 5 wherein the additive is a chemotherapeutic agent.

10. The composition of claim 5 wherein the additive is a lipophilic drug.

11. The composition of claim 5 wherein the additive is a chemotherapeutic protective agent.

12. The composition of claim 5 wherein the additive is a radioprotective agent.

13. The composition of claim 5 wherein the additive is a mixture of a chemotherapeutic agent and a chemotherapeutic protective agent.

14. The composition of claims 11, 12, or 13 wherein the protective agent is WR-2721.

15. The composition of claim 9 wherein the agent is methotrexate.

16. The composition of claim 9 wherein the agent is cyclophosphamide.

17. The composition of claim 10 wherein the drug is Vincristine.

18. The composition of claim 10 wherein the drug is Daunomycin.

19. The composition of claim 5 which further comprises a dispersant.

20. The composition of claim 19 wherein the dispersant is a condensate of ethylene oxide and an adduct of propylene oxide and propylene glycol, or a fluorinated amidoamine oxide.

21. The composition of claim 5 which further comprises a radiopaque agent.

22. The composition of claim 5 wherein the perfluorocarbon comprises a mixture of F-trimethylbicyclo[3.3.1]nonane and F-dimethyladamantane.

23. A method for producing an aqueous emulsion of a perfluorocarbon capable of carrying oxygen which comprises a two stage dispersion process wherein the perfluorocarbon is first dispersed in an aqueous solution of dispersant by blending said solution with sufficient energy to produce an emulsion of particle size 0.5 to 1 micron and the emulsion so formed is subsequently subjected to a further dispersion stage at higher energy levels sufficient to produce an emulsion of particle size 0.05 to 0.2 micron.

24. The method of claim 23 wherein the dispersant is a condensate of ethylene oxide and an adduct of proplyene oxide and propylene gylcol, or a fluorinated amidoamine oxide.

25. The method of claim 23 wherein the perfluorocarbon is presaturated with carbon dioxide.

26. The method of enhancing the therapeutic effectiveness of a lipophilic drug in an animal, which comprises administering to the animal a therapeutically effective amount of the drug in admixture with an emulsified perfluorocarbon capable of carrying oxygen or sequentially with administration of the drug.

27. The composition of claim 5 wherein said perfluorocarbon is perfluorinated methyl adamantane.

28. The composition of claim 5 wherein said perfluorocarbon is perfluorinated decalin.

29. The composition of claim 5 wherein said perfluorocarbon is perfluorinated 1-methyl octahydroquinolizine.

30. The composition of claim 19 wherein the dispersant is a phospholipid.

* * * * *

UNITED STATES PATENT OFFICE
CERTIFICATE OF CORRECTION

PATENT NO. : 4,742,050  Page 1 of 2

DATED : May 3, 1988

INVENTOR(S) : John M. Yuhas, deceased, Robert L. Goodman, Robert E. Moore

It is certified that error appears in the above-identified patent and that said Letters Patent are hereby corrected as shown below:

Column 14, line 7, for "um" substitute "$\mu$m"

Column 14, line 23, for "um" substitute "$\mu$m"

Column 15, line 25, for "um" substitute "$\mu$m"

Column 16, line 2, after "rather" insert "than"

Column 17, line 44, for "therapautic" substitute "therapeutic"

Column 17, line 49, for "uM" substitute "mM"

Column 17, line 60, for "um" substitute "$\mu$m"

Column 19, line 61, for "resistent" substitute "resistant"

Column 20, line 48, after "example," insert "by"

Claim 24, lines 2 and 3, for "proplyene" substitute "propylene"

UNITED STATES PATENT OFFICE
CERTIFICATE OF CORRECTION

PATENT NO. : 4,742,050
DATED : May 3, 1988
INVENTOR(S) : John M. Yuhas, deceased, Robert L. Goodman, Robert E. Moore It is certified that error appears in the above-identified patent and that said Letters Patent are hereby corrected as shown below:

Column 14, line 39, for "dispersion" substitute "dispersions"

Column 15, line 67, for "hypervolemeically" substitute "hypervolemically"

Column 19, line 22, after "experiment" insert "and"

Column 20, line 38, for "dispersion" substitute "dispersions"

Column 21, line 26, for "An" substitute "And"

Claim 3, line 1, for "in" substitute "is"

Signed and Sealed this

Eleventh Day of October, 1988

Attest:

DONALD J. QUIGG

*Attesting Officer*  *Commissioner of Patents and Trademarks*

UNITED STATES PATENT OFFICE
CERTIFICATE OF CORRECTION

PATENT NO. : 4,742,050
DATED : May 3, 1988
INVENTOR(S) : John M. Yuhas, deceased, Robert L. Goodman, Robert E. Moore It is certified that error appears in the above-identified patent and that said Letters Patent is hereby corrected as shown below:

Claim 26, line 6, for "drug" substitute "perfluorocarbon"

Signed and Sealed this

Twenty-second Day of August, 1989

Attest:

DONALD J. QUIGG

*Attesting Officer*  *Commissioner of Patents and Trademarks*

REEXAMINATION CERTIFICATE (2322nd)

United States Patent [19]

Yuhas, deceased et al.

[11] B1 4,742,050

[45] Certificate Issued Jun. 28, 1994

[54] SENSITIZATION OF HYPOXIC TUMOR CELLS AND CONTROL OF GROWTH THEREOF

[75] Inventors: John M. Yuhas, deceased, late of Bala Cynwyd, by Mary Ellen Yuhas, administrator; Robert L. Goodman, Gladwyne, all of Pa.; Robert E. Moore, Wilmington, Del.

[73] Assignee: Alpha Therapeutic Corporation, Los Angeles, Calif.

Reexamination Request:
No. 90/001,840, Sep. 11, 1989

Reexamination Certificate for:
Patent No.: 4,742,050
Issued: May 3, 1988
Appl. No.: 96,298
Filed: Sep. 9, 1987

Related U.S. Application Data

[60] Continuation of Ser. No. 724,445, Apr. 17, 1985, abandoned, Division of Ser. No. 580,760, Feb. 17, 1984, abandoned, which is a continuation-in-part of Ser. No. 517,150, Jul. 25, 1983, abandoned, which is a continuation-in-part of Ser. No. 408,589, Aug. 17, 1982, abandoned.

[51] Int. Cl.⁵ ............................................. A61K 31/70
[52] U.S. Cl. ....................................................... 514/34

[56] References Cited

U.S. PATENT DOCUMENTS

| | | | |
|---|---|---|---|
| 3,453,333 | 7/1969 | Litt et al. | 260/614 |
| 3,778,381 | 12/1973 | Rosano et al. | 424/342 |
| 3,828,085 | 8/1974 | Price et al. | 424/320 |
| 4,241,060 | 12/1980 | Smithen | 424/248.57 |
| 4,282,232 | 8/1981 | Agrawal | 424/267 |
| 4,325,972 | 4/1982 | Geyer et al. | 424/325 |
| 4,366,169 | 12/1982 | White | 424/285 |
| 4,452,818 | 6/1984 | Haidt | 424/352 |

*Primary Examiner*—Jerome Massie

[57] ABSTRACT

Method of sensitizing hypoxic tumor cells to radiotherapy and chemotherapy by contacting the cells or the vasculature thereof with an aqueous dispersion of an oxygen carrying perfluoro compound and a dispersant for the compound, and sensitizing chemotherapeutic and protective compositions therefor.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 5-25, 27-30 is confirmed.

Claims 1 and 26 are determined to be patentable as amended.

Claims 2-4, dependent on an amended claim, are determined to be patentable.

1. A method of delivering a lipophilic drug in an animal, comprising administering to the animal *in the presence of blood* a therapeutically effective amount of the drug in an aqueous dispersion of a perfluoro compound capable of carrying oxygen.

26. The method of enhancing the therapeutic effectiveness of a lipophilic drug in an animal, which comprises administering to the animal *in the presence of blood* a therapeutically effective amount of the drug in admixture with an emulsified perfluorocarbon capable of carrying oxygen or sequentially with administration of the [drug] *perfluorocarbon*.

* * * * *